(12) United States Patent
Nencioni et al.

(10) Patent No.: US 11,963,941 B2
(45) Date of Patent: Apr. 23, 2024

(54) USE OF A FASTING MIMICKING DIET TO ENHANCE THE EFFICACY OF ANTIESTROGENS IN CANCER

(71) Applicants: UNIVERSITA' DEGLI STUDI DI GENOVA, Genoa (IT); L-NUTRA INC., Culver City, CA (US)

(72) Inventors: Alessio Nencioni, Genoa (IT); Alberto Ballestrero, Genoa (IT); Patrizio Odetti, Genoa (IT); Fiammetta Monacelli, Genoa (IT); Irene Caffa, Alassio (IT); Valter Longo, Culver City, CA (US)

(73) Assignees: UNIVERSITA' DEGLI STUDI DI, Genoa (IT); L-NUTRA INC., Culver City, CA (US)

( * ) Notice: Subject to any disclaimer, the term of this patent is extended or adjusted under 35 U.S.C. 154(b) by 268 days.

(21) Appl. No.: 16/075,187

(22) PCT Filed: Feb. 14, 2017

(86) PCT No.: PCT/EP2017/053209
§ 371 (c)(1),
(2) Date: Aug. 3, 2018

(87) PCT Pub. No.: WO2017/140641
PCT Pub. Date: Aug. 24, 2017

(65) Prior Publication Data
US 2019/0038591 A1 Feb. 7, 2019

(30) Foreign Application Priority Data

Feb. 18, 2016 (IT) .......................... 102016000017036

(51) Int. Cl.
| | | |
|---|---|---|
| *A61K 31/337* | (2006.01) | |
| *A61K 31/138* | (2006.01) | |
| *A61K 31/565* | (2006.01) | |
| *A61K 31/704* | (2006.01) | |
| *A61K 45/06* | (2006.01) | |
| *A61P 35/00* | (2006.01) | |

(52) U.S. Cl.
CPC .......... *A61K 31/337* (2013.01); *A61K 31/138* (2013.01); *A61K 31/565* (2013.01); *A61K 31/704* (2013.01); *A61K 45/06* (2013.01); *A61P 35/00* (2018.01)

(58) Field of Classification Search
CPC .. A61K 31/337; A61K 31/138; A61K 31/565; A61K 31/704; A61K 45/06; A61P 35/00
See application file for complete search history.

(56) References Cited

U.S. PATENT DOCUMENTS 7,563,583 B2 * 7/2009 Ballinger ................ A61P 43/00
435/7.1

FOREIGN PATENT DOCUMENTS

| WO | 2008119077 A1 | 10/2008 |
|---|---|---|
| WO | 2015134837 A2 | 9/2015 |

OTHER PUBLICATIONS

Dyczk et al. Systemic treatment of disseminated HER2-neatvie breast cancer. Current Gynecologic Oncology, vol. 9 No. 4, pp. 238-244, abstract (Year: 2011).*
Katzung & Trevor's Pharmacology: Examination & Board Review, 10th Edition, Chapter 54: Cancer Chemotherapy. Copyright by The McGraw-Hill Companies (Year: 2013).*
Abotaleb et al., Chemotherapeutic agents for the treatment of metastatic breast cancer: An update. Biomedicine & Pharmacotherapy, bol. 101, p. 458-477 (Year: 2018).*
Caffa I., et al., "Fasting potentiates the anticancer activity of tyrosine kinase inhibitors by strengthening MAPK signaling inhibition", Oncotarget, vol. 6, No. 14, Mar. 18, 2015, pp. 11820-11832.
Chen K., et al., "Caloric restriction mimetic 2-deoxyglucose antagonizes doxorubicin-induced cardiomyocyte death by multiple mechanisms", Journal of Biological Chemistry, vol. 286, No. 25, Jun. 24, 2011, pp. 21993-22006.
Laviano A., et al., "Toxicity in chemotherapy—when less is more", New England Journal of Medicine, vol. 366, No. 24, Jun. 14, 2012, pp. 2319-2320.
Lee C., et al., "Fasting cycles retard growth of tumors and sensitize a range of cancer cell types to chemotherapy", Science Translation Medicine, American Association for the Advancement of Science, vol. 4, No. 124-127, Mar. 7, 2012, pp. 74-83.
Safdie F. et al., "Fasting and cancer treatment in humans: a case series report", Aging, Impact Journals LLC US vol. 1, No. 12, Dec. 1, 2009, pp. 988-1007.
Search Report and Written Opinion of PCT/EP2017/053209 dated May 29, 2017.

* cited by examiner

*Primary Examiner* — Barbara P Badio
(74) *Attorney, Agent, or Firm* — Silvia Salvadori, P.C.; Silvia Salvadori (57) ABSTRACT

A compound having antiestrogenic activity is used in a method for the treatment of BC or other estrogen-responsive tumors in a human patient, wherein the method comprises subjecting the patient to a fasting mimicking diet for a period of 24-190 hours while the patient is being treated with the compound having antiestrogenic activity, which can be a selective estrogen receptor modulator (SERM), a selective estrogen receptor downregulator (SERD) or an aromatase inhibitor (AI).

11 Claims, 8 Drawing Sheets

| Pathway name | Entities found | Entities Total | Entities ratio | Entities pValue | Entities FDR | Reactions found | Reactions total | Reactions ratio | log2 Fold Change |
|---|---|---|---|---|---|---|---|---|---|
| Cell Cycle | 102 | 598 | 0.056 | 1.11E-16 | 1.29E-13 | 236 | 348 | 0.04 | -1.187 |
| Cell Cycle, Mitotic | 90 | 497 | 0.047 | 3.33E-16 | 1.93E-13 | 185 | 272 | 0.032 | -1.167 |
| DNA strand elongation | 20 | 39 | 0.004 | 1.21E-11 | 3.52E-09 | 15 | 16 | 0.002 | -1.677 |
| Unwinding of DNA | 12 | 12 | 0.001 | 1.03E-10 | 1.99E-08 | 4 | 4 | 0 | -1.819 |
| DNA Replication | 32 | 118 | 0.011 | 1.72E-10 | 2.84E-08 | 42 | 48 | 0.006 | -1.645 |
| Activation of ATR in response to replication stress | 18 | 39 | 0.004 | 6.64E-10 | 9.62E-08 | 7 | 9 | 0.001 | -1.601 |
| Mitotic G1-G1/S phases | 33 | 139 | 0.013 | 2.34E-09 | 3.00E-07 | 45 | 53 | 0.006 | -1.663 |
| G2/M Checkpoints | 26 | 92 | 0.009 | 3.85E-09 | 4.47E-07 | 13 | 19 | 0.002 | -1.159 |
| Homology Directed Repair | 31 | 128 | 0.012 | 4.55E-09 | 4.78E-07 | 41 | 50 | 0.006 | -1.074 |
| Chromosome Maintenance | 27 | 101 | 0.009 | 6.11E-09 | 5.87E-07 | 20 | 27 | 0.003 | -0.439 |
| S Phase | 32 | 140 | 0.013 | 9.84E-09 | 8.76E-07 | 41 | 52 | 0.006 | -1.585 |
| HDR through Homologous Recombination (HR) or Single Strand Annealing (SSA) | 29 | 122 | 0.011 | 2.12E-08 | 1.74E-06 | 37 | 42 | 0.005 | -1.055 |

USE OF A FASTING MIMICKING DIET TO ENHANCE THE EFFICACY OF ANTIESTROGENS IN CANCER

This application is a U.S. national stage of PCT/EP2017/053209 filed on 17 Feb. 2017, which claims priority to and the benefit of Italian Patent Application No. 102016000017036 filed on 18 Feb. 2016, the contents of which are all incorporated herein by reference in their entireties.

TECHNICAL FIELD

The present invention concerns the technical field of the pharmaceutical industry.

In particular, the invention relates to compounds having antiestrogenic activity, including selective estrogen receptor modulators (SERMs), selective estrogen receptor down-regulators (SERDs) and aromatase inhibitors (AIs), for use in the treatment of breast cancer (BC) and other estrogen sensitive cancers in association with a defined dietetic regimen.

PRIOR ART

Over 200,000 women present every year with BC in the U.S [1]. About 70% of all BCs express the estrogen receptor (ER). Commonly used therapies to treat these cancers either target the ER directly through SERMs (e.g., tamoxifen) and SERDs (fulvestrant), or diminish endogenous estrogen levels by ovarian ablation or AIs. However, the emergence of hormone therapy resistance remains a major issue, as almost 40% of women with metastatic, ER-positive disease progress despite the initial efficacy [2], [3]. Multiple mechanisms account for endocrine resistance, including deregulation of components of the ER signalling pathway, alterations in cell cycle and pro-survival signalling molecules, and activation of growth-promoting signalling cascades (e.g. phosphatidylinositol 3-kinase (PI3K)/Akt/mammalian target of rapamycin (mTOR)) [2], [4].

Some strategies have allowed to improve the effect of hormone therapy in BC and/or to reinstate the activity of these hormone drugs once resistance has appeared.

Inhibition of mTOR was shown to reinstate sensitivity to hormone therapy both experimentally and clinically and the combination of the steroidal AI exemestane with everolimus (an mTOR inhibitor) is now FDA-approved for patients with metastatic ER-positive BC recurring or progressing after treatment with letrozole or anastrozole (NCCN Guidelines Version 3.2015) [5]. More recently, in the first-line setting, the addition of the CDK4/6 inhibitor palbociclib to the AI letrozole has also proved successful, resulting in drug approval [6]. However, despite this progress, there remains a critical need to identify safe and cost-effective approaches that increase the effectiveness of hormone therapy in ER-positive BC avoiding or at least delaying the occurrence of resistance.

Recent studies show that the use of short periods of fasting or fasting-mimicking diets sensitize cancer cells to the following antineoplastic treatments: chemotherapeutics, tyrosine kinase inhibitors and radiotherapy [7], [8], [9], [10]. Such sensitizing effects have been documented both in vitro and in vivo. In the latter case, this effect is obtained by means of starvation (only water) or by means of specifically designed hypocaloric diets (fasting-mimicking diets).

This ability of fasting or fasting-mimicking diets to enhance the activity of antineoplastic agents essentially reflects the inability of malignant cells to adapt to nutrient deprivation, primarily due to the aberrant activation of growth promoting signaling cascades (resulting, in turn, from mutations in oncogenes, such as RAS, HER2, EGFR and AKT, or in tumor suppressors, such as PTEN), and to increased p53 activation in response to starvation in cancer cells (via relief of REV1's inhibition of p53 itself) [11].

Vice versa, non-transformed tissues remain unaffected, or may even benefit from a fasting or fasting-mimicking diets by reverting to a self-protection mode characterized by reduced cell growth, increased sirtuin activity, and autophagy activation, thus becoming more resistant to genotoxic stress and able to tolerate doses chemotherapeutics that would otherwise be lethal for non-starved cells [12], [13], [14], [15]. Notably, fasting or fasting-mimicking diets are also effective at increasing the activity of commonly employed tyrosine kinase inhibitors, suggesting that even more modern, molecularly targeted treatments may strongly benefit from co-administration with regimens of periodic fasting or fasting-mimicking diets [10].

The discovery that fasting or fasting-mimicking diets increase the efficacy of chemotherapy in cancer cells while at the same time shielding healthy cells from its toxicity has recently attracted strong attention amongst physicians [16] and patients, and several pilot trials are currently exploring fasting or fasting-mimicking diets in combination with chemotherapy in humans (including studies performed at the USC Norris Comprehensive Cancer Center, University of Leiden, University of Genoa and Charitè University in Berlin (NCT01304251, NCT01175837, NCT00936364, NCT01175837, NCT01802346, NCT02126449). These studies consistently confirm the findings of Safdie et al. [17], indicating that starvation during chemotherapy is well tolerated and virtually without side effects. In addition, cycles of fasting or of fasting-mimicking diets have been shown to protect bone marrow cells from the toxicity of chemotherapy but also to promote the stem cell-based regeneration of progenitor and immune cells killed by cyclophosphamide treatment [18].

Nevertheless, no reliable forecasts can be made on the effects that fasting (or reduced-calorie diets) may have on the efficacy of an anticancer therapy based on compounds having antiestrogenic activity. By the expression "compounds having antiestrogenic activity" the following compounds are meant: SERMs, SERDs, and AIs.

For these reasons, the research carried out by the Applicant focused on the investigation of the possible interaction between starvation or reduced-calorie diets and an anticancer therapy based on compounds having antiestrogenic activity.

The present invention is the result of the above research activity.

SUMMARY OF THE INVENTION

In an aspect thereof, the present invention relates to a compound having antiestrogenic activity for use in a method for the treatment of BC or other estrogen-responsive tumors and cancers in a human patient, wherein the method comprises subjecting said patient to reduced caloric intake for a period of 24-190 hours while said patient is being treated with said compound having antiestrogenic activity.

The above-mentioned compound having antiestrogenic activity is preferably selected among the group consisting of SERMs, SERDs, and of AIs.

By reduced caloric intake it is hereby meant a daily caloric intake reduced by 10-100%, preferably by 50-100%, more preferably by 75-100%, with respect to the regular caloric intake, including total starvation.

The subject's regular caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women.

Preferably, when the daily caloric intake is reduced by 10-85%, the patient is fed with foods with a high content of monounsaturated and polyunsaturated fats and a reduced content of proteins and sugars (40% of calories coming from fat). This because a diet based on such foods has beneficial effects that are similar to those of starvation [13].

Preferably said period of reduced caloric intake ranges from 48 to 150 hours, and most preferably it is of about 120 hours.

Among the SERMs that can be used in the present invention, the following are mentioned: tamoxifen, raloxifene, toremifene, lasofoxifene, ospemifene, arzoxifene, bazedoxifene.

Among the SERDs that can be used in the present invention, the following are mentioned: fulvestrant, RU 58668, GW7604, GDC-0810, AZD9496, pipendoxifene, acolbifene, OP-1074 ((2S)-3-(4-hydroxyphenyl)-4-methyl-2-(4-{2-[(3R)-3-methylpyrrolidin-1-yl]ethoxy}phenyl)-2H-chromen-7-ol).

Among the AIs that can be used in the present invention, the following are mentioned: anastrozole, exemestane, letrozole, vorozole, formestane, fadrozole.

As used herein, "cancer" refers to a disease or disorder characterized by uncontrolled division of cells and the ability of these cells to spread, either by direct growth into adjacent tissue through invasion, or by implantation into distant sites by metastasis. The present invention is focused on the treatment of BC, in particular ER-positive BC but it applies to all estrogen-responsive tumors and cancers.

The above-mentioned period of reduced caloric intake with concurrent administration of the compound having antiestrogenic activity to the patient can be repeated one or more times after respective periods of 5-60 days, during which the patient is given the antiestrogenic compound while following a diet involving a regular caloric intake.

The above-mentioned reduced calorie intake regimen preferably corresponds to less than 800 kcal/day, more preferably 400 Kcal/day.

Such reduced caloric intake can be obtained by means of dietetic foods with reduced caloric, sugar, and protein content, but containing relatively high levels of unsaturated "good fats" and all necessary micronutrients to prevent malnutrition.

In another aspect, the present invention relates to a compound having antistrogenic activity as defined above for the use in a method of treating BC in a human patient, in which the human patient, while being treated with the compound having antiestrogenic activity, is additionally treated with a chemoterapeutic agent, which is preferably selected among the group consisting of taxanes, preferably docetaxel and paclitaxel, cyclophosphamide, methotrexate, 5-fluorouracil, gemcitabine, vinorelbine, carboplatin, cisplatin, epirubicin and doxorubicin.

In another aspect, the present invention relates to a pharmaceutical composition comprising a compound with antiestrogenic activity as defined above and a pharmaceutically acceptable carrier for use in the method for the treatment of BC and other estrogen-dependent tumors and cancers in a patient as defined above.

The pharmaceutical composition according to the present invention can further comprise a chemoterapeutic agent, which is preferably selected among the group consisting of taxanes, preferably docetaxel and paclitaxel, cyclophosphamide, methotrexate, 5-fluorouracil, gemcitabine, vinorelbine, carboplatin, cisplatin, epirubicin and doxorubicin.

In a further aspect, the present invention relates to a method of treating a BC cell or a tumor cell responsive to estrogen with a compound having antiestrogenic activity, comprising:

cultivating a BC cell or a tumor cell responsive to estrogen in a medium with reduced serum or glucose concentration; and treating the cancer cell with a compound having antiestrogenic activity.

The serum concentration in the medium is preferably reduced by 10-90% and the glucose concentration in the medium is preferably reduced by 20-90%.

As it will become clear from the experimental results reported in the following sections, it has unexpectedly been found that starvation, in particular STS, and also a reduced caloric intake for periods of 24-72, positively affect the anticancer efficacy of a concurrent anticancer treatment with a compound having antiestrogenic activity.

A positive effect on the efficacy of a concurrent anticancer treatment with a compound having antiestrogenic activity is also obtained when the above mentioned periods of reduced caloric intake are replaced by corresponding periods of regular caloric intake, during which the patients are only fed with the above-mentioned foods with a high content of monounsaturated and polyunsaturated fats and a reduced content of proteins and sugars (≥40% of calories coming from fat), since a diet based on such foods has beneficial effects that are similar to those of starvation [10].

In an aspect thereof, the present invention thus also concerns a compound having antiestrogenic activity for use in a method for the treatment of cancer in a human patient, wherein the method comprises feeding said patient only with foods with a high content of monounsaturated and polyunsaturated fats and a reduced content of proteins and carbohydrates (≥40% of calories coming from fat), in such an amount as to ensure a regular daily caloric intake, for a period of 24-190 hours, while said patients is being treated with said compound having antiestrogenic activity.

Differently from what happened with the previously known treatments associating STS with chemotherapy or radiotherapy, which generally required the administration of a corticosteroid in order to counter the side effects (i.e. nausea) and allergic reactions caused by chemotherapy and radiotherapy, the method according to the present invention does not require the administration of corticosteroids, because compounds with antiestrogenic activity do not display the severe side effects of chemotherapy or radiotherapy.

This is quite a significant advantage over the above-mentioned known treatments, because the metabolic adaptations to starving (e.g. hypoglycemia, low IGF-1 and insulin plasma levels), which are beneficial in terms of response by the tumor cells, are not prevented or hindered by a concomitant administration of corticosteroids.

In addition, with respect to the strategies mentioned above that improve the effect of hormone therapy in BC and/or reinstate the activity of these hormone drugs once resistance has appeared by administering mTOR inhibitors, such as everolimus, or a CDK4/6 inhibitor, such as palbociclib, the treatment proposed with the present invention achieves the same effects, while being well tolerated and devoid of severe side effects. The treatment hereby proposed is even potentially capable of reducing the side effects of the hormone therapy itself and of promoting regenerative effects, whereas everolimus and palbociclib can both cause significant side effects, such as stomatitis, anemia and hyperglycemia [5], in the case of everolimus, and neutropenia and lung thromboembolism, in the case of palbociclib [6].

The compounds and compositions according to the invention may be administered with any available and efficient delivery system, comprising, but not limited to, oral, buccal, parenteral, inhalatory routes, topical application, by injection, by transdermic or rectal route (for ex. by means of suppositories) in dosage unit formulations containing conventional, pharmaceutically acceptable and non-toxic carriers, adjuvants and vehicles. The administration by parenteral route comprises subcutaneous, intravenous, intramuscular, intrasternal injection or infusion techniques.

The solid dosage forms for the administration by oral route comprise, for example, capsules, tablets, powders, granules and gels. In such solid dosage forms, the active compound may be mixed with at least one inert diluent such as, for example, sucrose, lactose or starch. These dosage forms normally also comprise additional substances different from the inert diluents, such as, for example, lubricating agents like magnesium stearate.

The injectable preparations, for example aqueous or oily sterile injectable solutions or suspensions, may be formulated according to the known technique and by optionally using appropriate dispersing, wetting and/or suspending agents.

The pharmaceutical preparations according to the present invention may be produced by using conventional pharmaceutical techniques, as described in the various pharmacopoeias or handbooks of the field such as, for example, "Remington's Pharmaceutical Sciences Handbook", Mack Publishing, New York, 18th Ed., 1990.

The average daily dosage of the compounds according to the present invention depends on many factors, such as, for example, the seriousness of the disease and the conditions of the patient (age, weight, sex): The dose may generally vary from 1 mg to 1500 mg per day of compound according to the invention, optionally divided into more administrations.

The present invention will be further described with reference to the appended drawings and to certain embodiments, which are provided here below by way of illustration and not of limitation.

BRIEF DESCRIPTION OF THE DRAWINGS

2) the respective effects of fasting mimicking conditions or of a fasting-mimicking diet (1% fetal calf serum and 50 mg/dl glucose–FMD), tamoxifen (5 μM), FMD+ tamoxifen (5 μM), tamoxifen 5 μM+taxotere 100 nM, FMD+taxotere 100 nM, FMD+tamoxifen 5 μM+taxotere 100 nM on the viability of the ER-positive BC cells MCF7.

DETAILED DESCRIPTION

Figure 1:
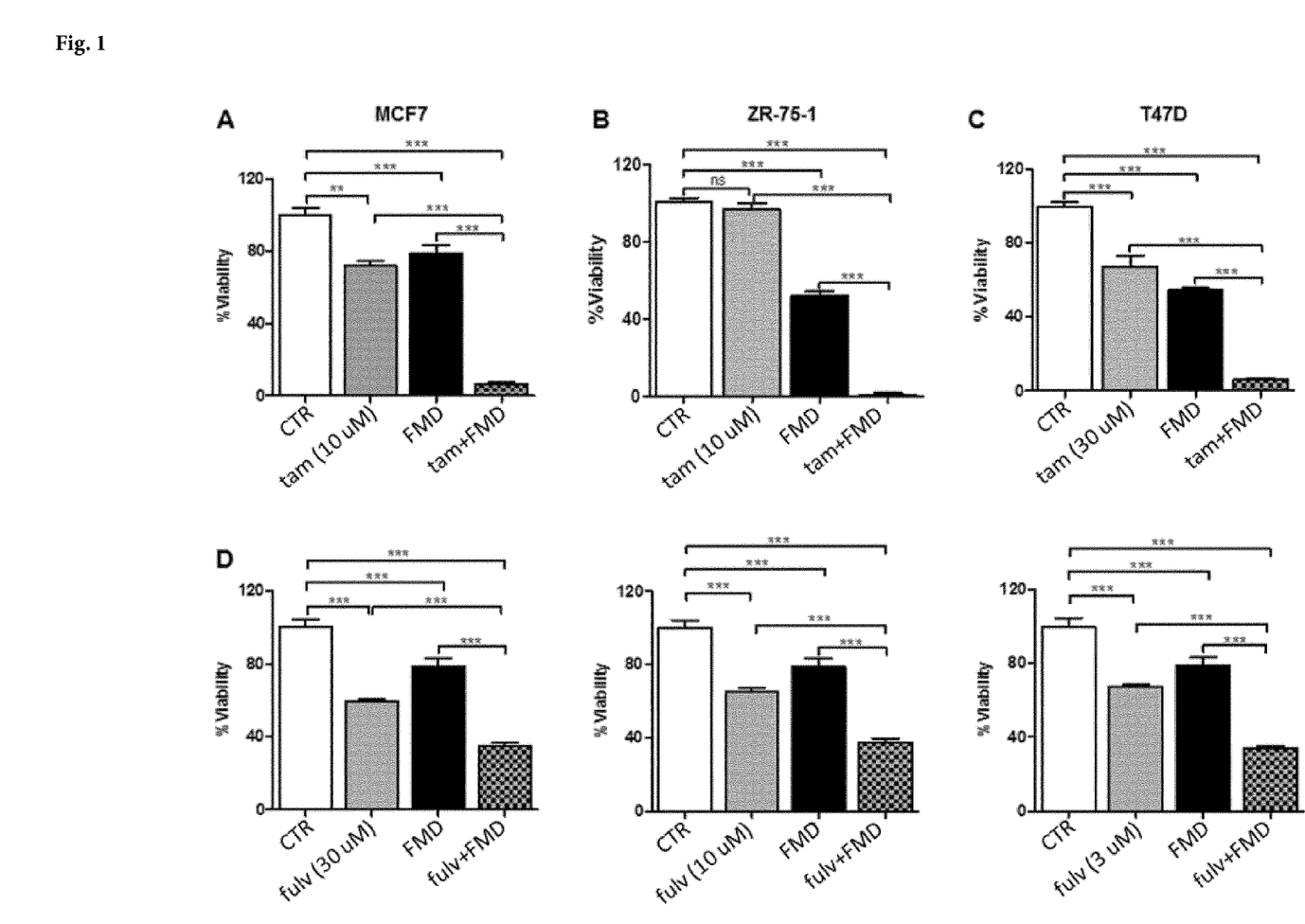
FIG. 1A is a histogram showing the respective effects of fasting mimicking conditions (conditions recreating the metabolic consequences of fasting in the blood) or of a fasting-mimicking diet (1% fetal calf serum and 50 mg/dl glucose–FMD), tamoxifen, and FMD+tamoxifen on the viability of the ER-positive BC cells MCF7.
FIG. 1B is a histogram showing the respective effects of fasting mimicking conditions or of a fasting-mimicking diet (1% fetal calf serum and 50 mg/dl glucose–FMD), tamoxifen, and FMD+tamoxifen on the viability of the ER-positive BC cells ZR-75-1.
FIG. 1C is a histogram showing the respective effects of fasting mimicking conditions or of a fasting-mimicking diet (1% fetal calf serum and 50 mg/dl glucose–FMD), tamoxifen, and FMD+tamoxifen on the viability of ER-positive BC cells T47D.
FIG. 1D comprises three histograms showing the respective effects of fasting mimicking conditions or of a fasting-mimicking diet (1% fetal calf serum and 50 mg/dl glucose–FMD), fulvestrant, and FMD+fulvestrant on the viability of ER-positive BC cells MCF7, at three different concentrations of fulvestrant.

The Applicants performed several experiments to assess whether fasting mimicking conditions or a fasting-mimicking diet (1% fetal calf serum and 50 mg/dl glucose–FMD) would sensitize BC cells to tamoxifen and to fulvestrant. Indeed, a strong potentiation of tamoxifen activity by FMD conditions (FIG. 1A-C) was detected in all of the cellular models of ER-positive BC tested (MCF7, ZR-75-1, T47D). Similarly, a marked increase in fulvestrant's anti-proliferative effects in MCF7 cells could be readily shown (FIG. 1D).

In particular, in the experiments of FIGS. 1A-D, $3 \times 10^3$ MCF7 (A, D), ZR-75-1 (B) or T47D (C) cells were plated in 96 well plates in regular DMEM medium containing 10% FBS. 24 h later, the cell medium was removed and cells were incubated for 24 h either in the same medium (CTR) or in low-glucose (0.5 g/L) DMEM medium containing 1% FBS (FMD). 24 h later, tamoxifen (Tam) or fulvestrant (Fulv) at the indicated concentrations were added to the culture medium.

Subsequent experiments were aimed at defining the mechanisms underlying the potentiation of tamoxifen's and fulvestrant's activity in BC cell lines by fasting mimicking conditions or of a fasting-mimicking diet (FMD). These experiments showed that FMD conditions essentially increased the ability of tamoxifen and of fulvestrant to induce a G1 cell cycle arrest (FIG. 2A-C).

Interestingly, this correlated with a reduction in Rb phosphorylation (Ser780, not shown) and in a downregulation of cell cycle promoting genes (E2F1, E2F2 and CCNE1) that was more pronounced in response to fasting mimicking conditions or of a fasting-mimicking diet (FMD) combined with tamoxifen than in response the single treatments (effects that were observed in all of the cell lines) (FIG. 2D).

In particular, in the experiments of FIGS. 2A-D, $5 \times 10^5$ MCF7, ZR-75-1 or T47D cells were plated in 6-well plates in regular DMEM medium containing 10% FBS. 24 h later, the cell medium was removed and cells were incubated for 24 h either in the same medium (CTR) or in fasting mimicking conditions or a fasting mimicking diet (FMD). 24 h later, 10 μM tamoxifen (Tam) was added to the culture medium where indicated. 24 h later, cells were used for cell cycle analysis or for mRNA extraction and subsequent determination of E2F1, E2F4 and CCNE1 expression by QPCR.

In T47D cells, cell cycle arrest and E2F1, E2F2 and CCNE1 downregulation only occurred in response to a combined treatment with fasting mimicking conditions or a fasting-mimicking diet plus tamoxifen. Thus, these results clearly indicated that fasting or fasting mimicking diets have the potential to increase the ability of hormone therapies to block proliferation in ER-positive cell lines.

The Applicant subsequently investigated the effects of tamoxifen, fasting mimicking conditions or of a fasting-mimicking diet, and their combination on cell signaling, focusing in particular on the PI3K-mTOR pathway given its role in resistance to hormonal treatments in BC [2], [5].

Figure 3:
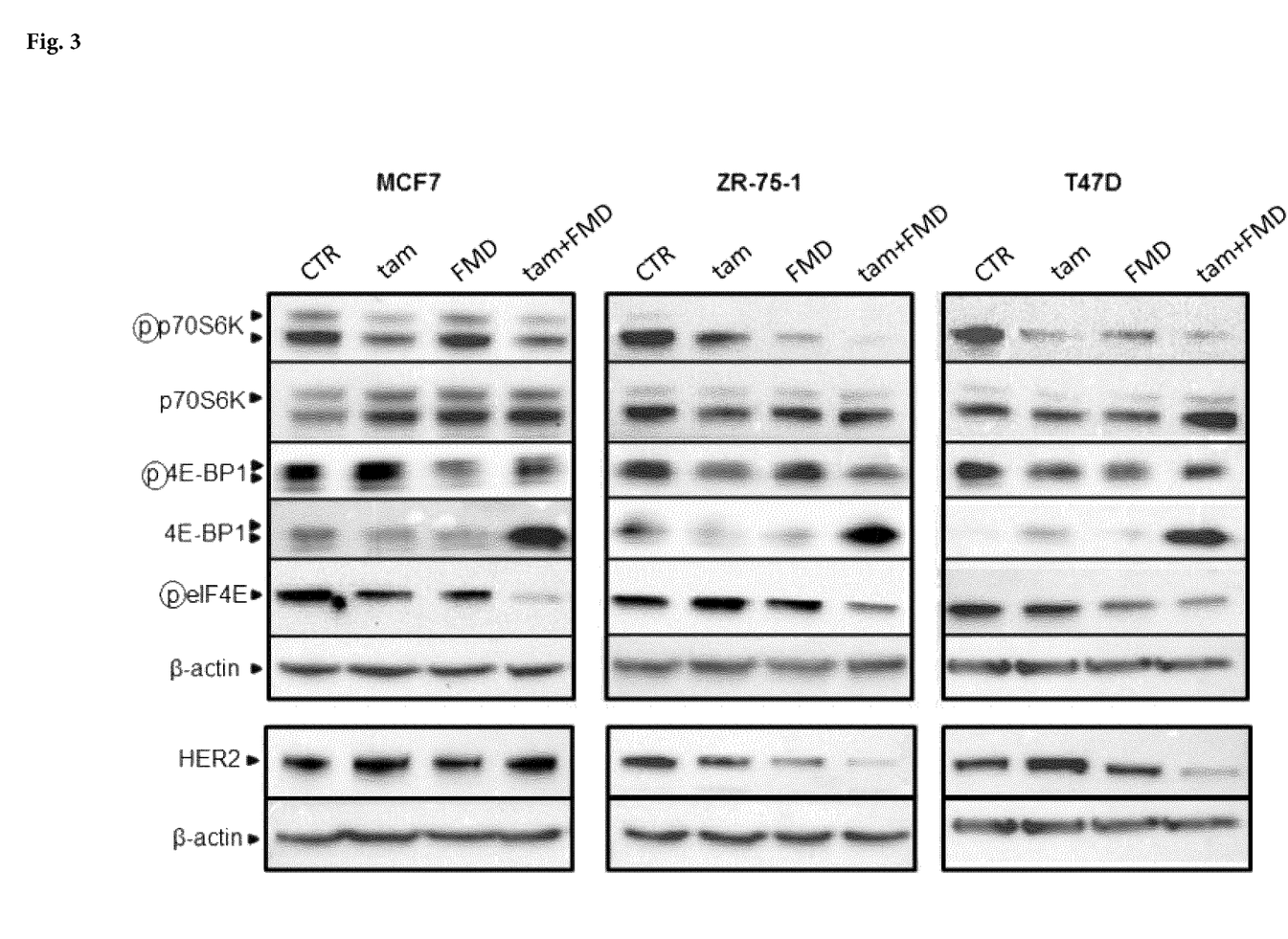
FIG. 3 is an immunoblotting showing the levels of total and phosphorylated p70S6K (Thr389, total and phosphorylated 4E-BP1, phosphorylated eIF4E (Ser209) and β-actin in cell lysates from MCF7, ZR-75-1 and T47D cells subjected to, respectively, fasting mimicking conditions or of a fasting-mimicking diet (1% fetal calf serum and 50 mg/dl glucose–FMD), treatment with tamoxifen, and FMD+treatment with tamoxifen.

Here it was of interest to observe that combining tamoxifen with fasting mimicking conditions or a fasting-mimicking diet (FMD) resulted in a marked inhibition of mTOR activity as detected by the reduced levels of phosphorylated p70S6K and eIF4E in MCF7, ZR-75-1, and T47D (FIG. 3).

Figure 2:
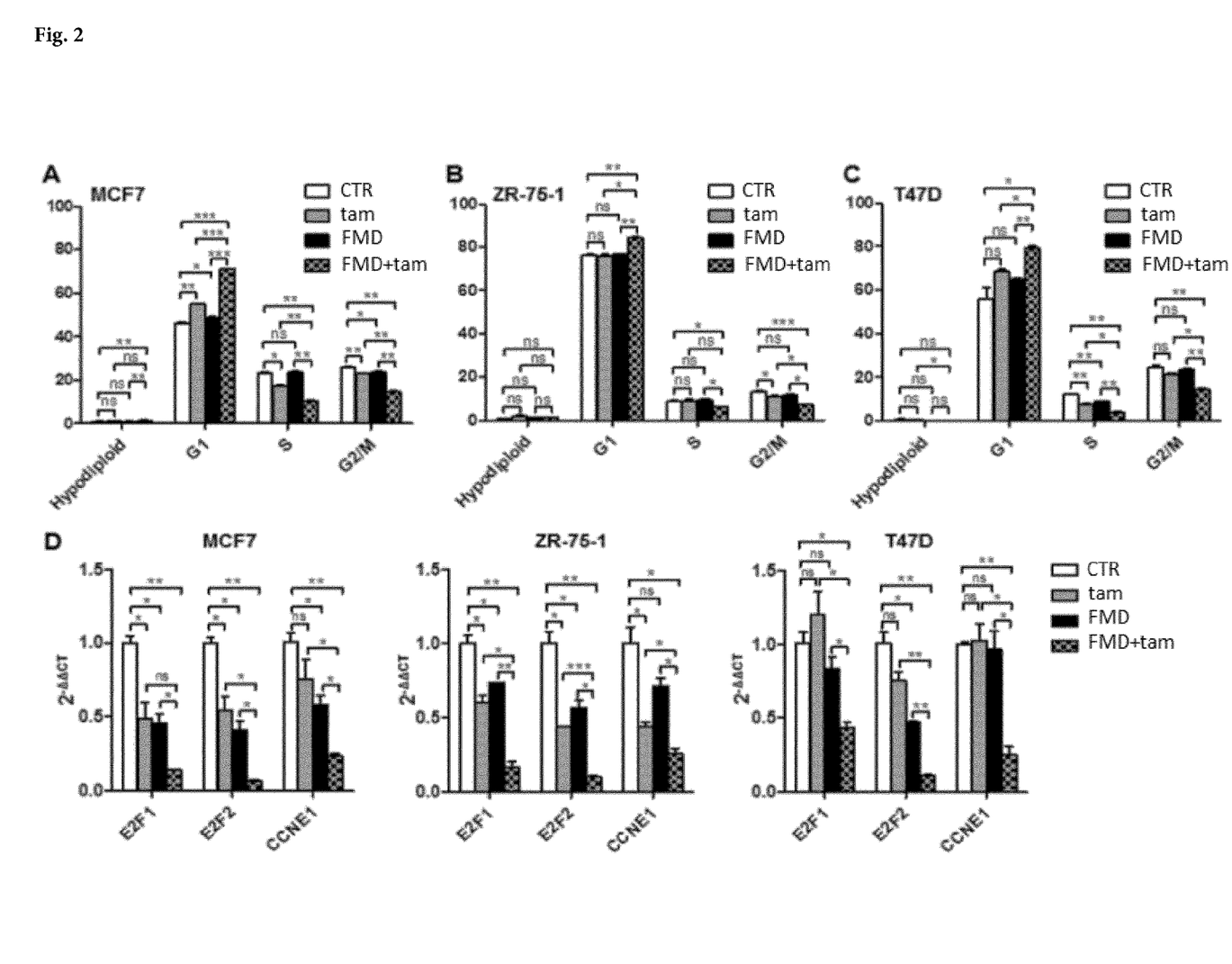
FIG. 2A is a histogram showing the respective effects fasting mimicking conditions or a fasting-mimicking diet (1% fetal calf serum and 50 mg/dl glucose–FMD), tamoxifen, and FMD+tamoxifen on the induction of a G1 cell cycle arrest in MCF7 cells.
FIG. 2B is a histogram showing the respective effects of fasting mimicking conditions or of a fasting-mimicking diet (1% fetal calf serum and 50 mg/dl glucose–FMD), tamoxifen, and FMD+tamoxifen on the induction of a G1 cell cycle arrest in ZR-75-1 cells.
FIG. 2C is a histogram showing the respective effects fasting mimicking conditions or of a fasting-mimicking diet (1% fetal calf serum and 50 mg/dl glucose–FMD), tamoxifen, and FMD+tamoxifen on the induction of a G1 cell cycle arrest in T47D cells.
FIG. 2D comprises three histograms showing the respective effects of fasting mimicking conditions or of a fasting-mimicking diet (1% fetal calf serum and 50 mg/dl glucose–FMD), tamoxifen, and FMD+tamoxifen on the expression of E2F1, E2F2 and CCNE1 genes in MCF7, ZR-75-1 and T47D cells.

In the experiment of FIG. 3, MCF7, ZR-75-1 and T47D cells were treated as in the experiment of FIG. 2. 24 h after tamoxifen (5 μM) addition, cells were used for protein lysate generation and total and phosphorylated p70S6K (Thr389), total and phosphorylated 4E-BP1, phosphorylated eIF4E (Ser209), HER2 and β-actin were detected by immunoblotting.

In the case of 4E-BP1 (a repressor of mRNA translation that is typically phosphorylated by mTOR, with consequent dissociation of 4E-BP1 from eIF4E and activation of cap-dependent mRNA translation), a marked accumulation of the unphosphorylated form in response to combined tamoxifen and fasting mimicking conditions or a fasting-mimicking diet (FMD) in all of the ER-positive cell lines was detected, which again is in line with impaired mTOR signalling.

Overall, these findings suggested that a block in protein translation may contribute to the strong anticancer activity of combined tamoxifen and fasting mimicking conditions or a fasting-mimicking diet (FMD).

In subsequent experiments, it was also evaluated whether addition of fasting mimicking conditions or a fasting-mimicking diet (FMD) to tamoxifen would affect the expression of HER2, whose upregulation has been implied as a mechanism of resistance to hormonal treatments in BC [2].

Noteworthy, in two out of three BC cell lines (ZR-75-1, and T47D), fasting mimicking conditions or a fasting-mimicking diet (FMD) led to a marked reduction in HER2 expression when applied in combination to tamoxifen (FIG. 3). Since HER2 signaling helps ER-positive BC cells resist hormone therapy, such an effect of fasting mimicking conditions or a fasting-mimicking diet (FMD) could well contribute to enhance BC cell susceptibility to hormone therapy itself [2].

Figure 4:
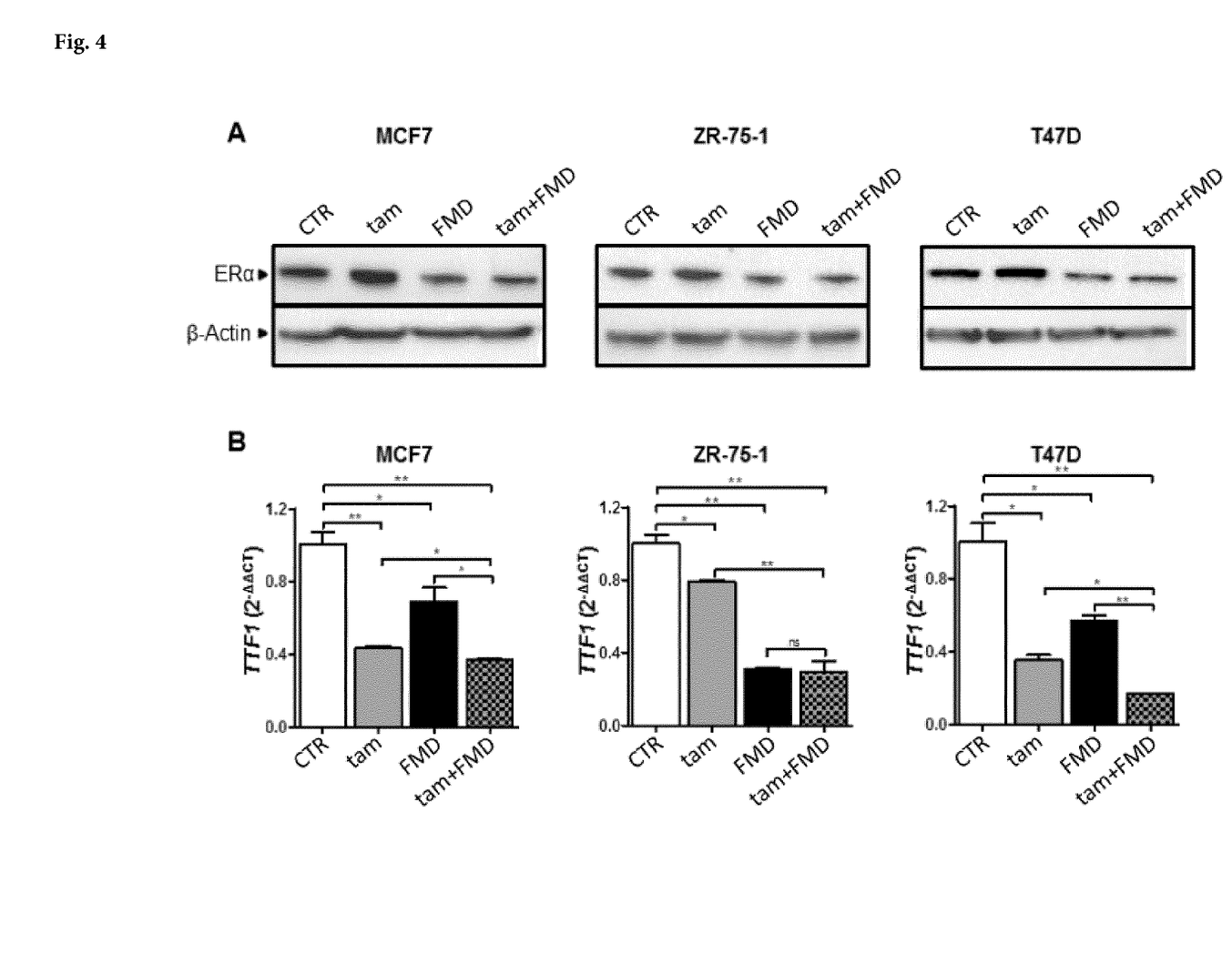
FIG. 4A is an immunoblotting showing the levels of ERα and β-actin in cell lysates from MCF7, ZR-75-1 and T47D cells subjected to fasting mimicking conditions or a fasting-mimicking diet (1% fetal calf serum and 50 mg/dl glucose–FMD), treatment with tamoxifen (5 µM), and FMD+treatment with tamoxifen (5 µM), respectively.
FIG. 4B includes three histograms showing the effects of, respectively fasting mimicking conditions or of a fasting-mimicking diet (1% fetal calf serum and 50 mg/dl glucose–FMD), tamoxifen, and FMD+tamoxifen on the expression of the TTF1 gene in MCF7, ZR-75-1 and T47D cells, as determined by QPCR.

Studies of ERα expression and of ERα-mediated transcription (QPCR detection of TTF1 expression) demonstrated that fasting mimicking conditions or a fasting-mimicking diet (FMD) reduce ERα levels and, consistently, increase the ability of tamoxifen to reduce TTF1 expression (FIG. 4).

In the experiment of FIG. 4, MCF7, ZR-75-1 or T47D cells were treated as in the experiment of FIG. 2. 24 h after tamoxifen (5 μM) addition, cells were used for protein lysate generation or for mRNA extraction, ER and β-actin were detected by immunoblotting. TTF1 expression was determined by QPCR.

Figure 5:
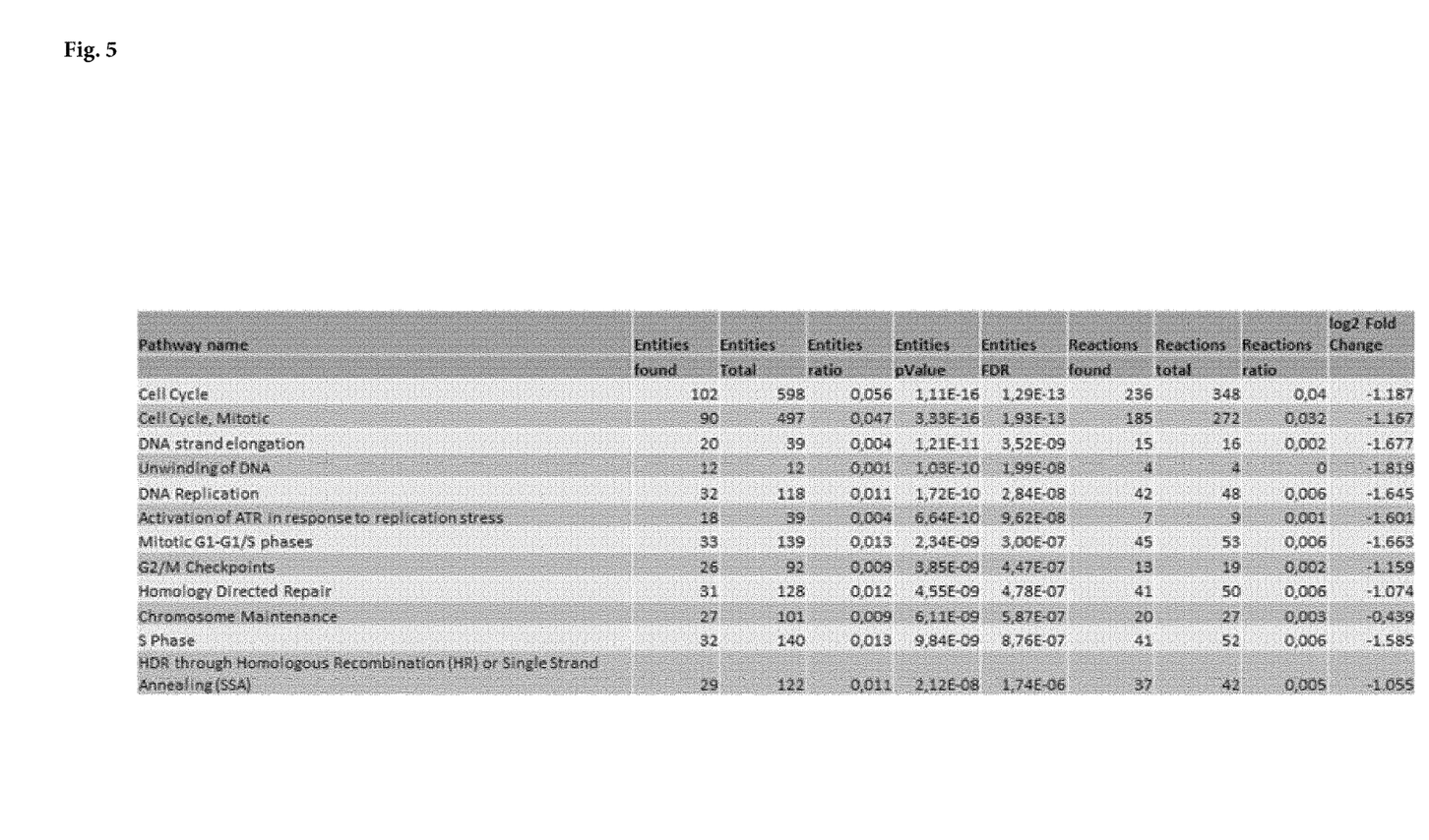
FIG. 5 is a table reporting a pathway analysis based on differentially expressed genes (DEGs) between fasting mimicking conditions or of a fasting-mimicking diet (1% fetal calf serum and 50 mg/dl glucose–FMD) vs. vehicle in MCF7 cells.

To gain further insights into the mechanisms underlying the potentiation of tamoxifen activity by fasting mimicking conditions or a fasting-mimicking diet (FMD), the effects of tamoxifen, of fasting mimicking conditions or of a fasting-mimicking diet (FMD), and their combination in terms of global gene expression on MCF7 cells, as detected by standard gene expression microarrays, were compared (data were extrapolated from 4 independent biological replicates/condition). According to a gene ontology (GO) analysis of the differentially expressed genes, it appeared that fasting mimicking conditions or a fasting-mimicking diet (FMD) and their combination with tamoxifen induced changes in gene expression that were similar, including similar effects on the cell cycle, DNA replication, unwinding of DNA, mitotic G1-G1/S phases pathways. Strikingly, however, the addition of fasting mimicking conditions or of a fasting-mimicking diet (FMD) to tamoxifen resulted in marked changes in pathways related to DNA repair that were not present in cells that were only exposed to fasting mimicking conditions or a fasting-mimicking diet (FMD), or to tamoxifen alone (FIG. 5).

RAD51 ($Log_2$ fold change: −1.864), PCNA ($Log_2$ fold change: −1.658), TIPIN ($Log_2$ fold change: −1.604), EXO1 ($Log_2$ fold change: −1.583), and BRCA1 ($Log_2$ fold change: −1.372) were the genes from these pathways that were found to be the most highly downregulated in MCF7 treated with tamoxifen and fasting mimicking conditions or a fasting-mimicking diet (FMD). As a validation of these data, a strong RAD51 downregulation in response to tamoxifen plus fasting mimicking conditions or a fasting-mimicking diet (FMD) in MCF7, ZR-75-1 and T47D cells was readily verified, both at the mRNA and at the protein level (FIG. 6A, B).

Figure 6:
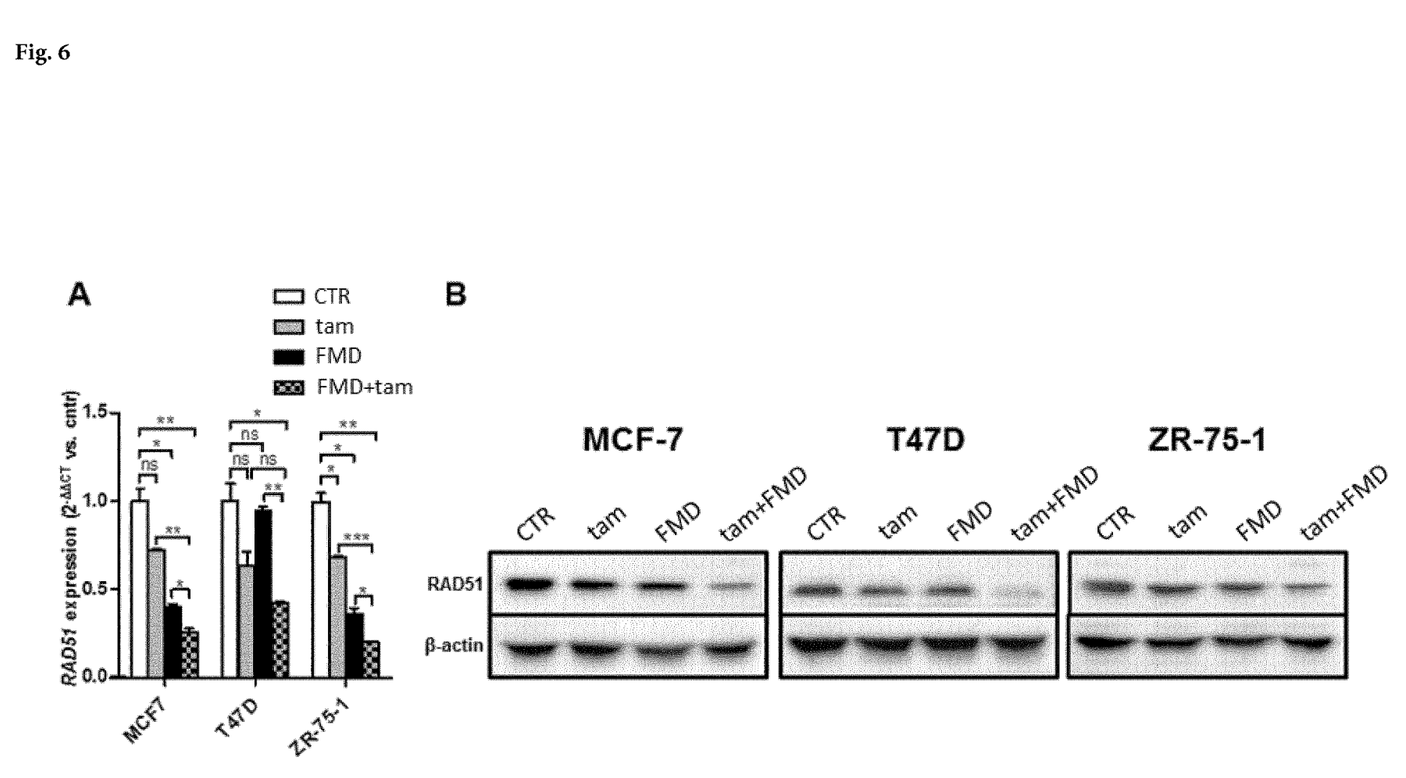
FIG. 6A includes three histograms showing the respective effects of fasting mimicking conditions or of a fasting-mimicking diet (1% fetal calf serum and 50 mg/dl glucose–FMD), tamoxifen, and FMD+tamoxifen on the expression of the RAD51 gene in MCF7, ZR-75-1 and T47D cells, as determined by QPCR.
FIG. 6B is an immunoblotting showing the levels of RAD51 and β-actin in cell lysates from MCF7, ZR-75-1 and T47D cells subjected to fasting mimicking conditions or of a fasting-mimicking diet (1% foetal calf serum and 50 mg/dl glucose–FMD), treatment with tamoxifen (5 µM), and FMD+treatment with tamoxifen (5 µM), respectively.

In the experiment of FIG. 6, MCF7, ZR-75-1 or T47D cells were treated as in the experiment of FIG. 2. 24 h after tamoxifen (5 μM) addition, cells were used for RNA extraction or for protein lysate generation. In FIG. 6A, RAD51 expression was detected by QPCR. In FIG. 6B, RAD51 and (β-actin were detected by immunoblotting.

A similar RAD51 downregulation was observed in MCF7 cells treated with combined fulvestrant and fasting mimicking conditions or a fasting-mimicking diet (FMD) (data not shown). Interestingly, an Ingenuity Pathway Analysis (IPA) revealed as a transcription factor highly likely to be mediating these changes in the gene expression profile of BC cells treated with combined tamoxifen and fasting mimicking conditions or a fasting-mimicking diet (FMD) (being inhibited by these stimuli combined with one another), FOXM1, a proto-oncogene involved in cell cycle progression, chromosomal segregation, and genomic stability [19].

Based on the data from the gene expression microarrays, indicating the impairment in the DNA repair ability of BC treated with tamoxifen plus fasting mimicking conditions or a fasting-mimicking diet (FMD), it was investigated whether, under these conditions, MCF7 cells would become more sensitive to chemotherapeutics. Specifically, two drugs that are commonly used for treating BC, taxotere (docetaxel) and doxorubicin were tested. Indeed, as detected in short-term viability assays (72 h), the triple treatment (tamoxifen plus doxorubicin or Taxotere plus fasting mimicking conditions or a fasting-mimicking diet (FMD)) was the one that achieved the most pronounced reduction in cell viability (FIG. 7).

Figure 7:
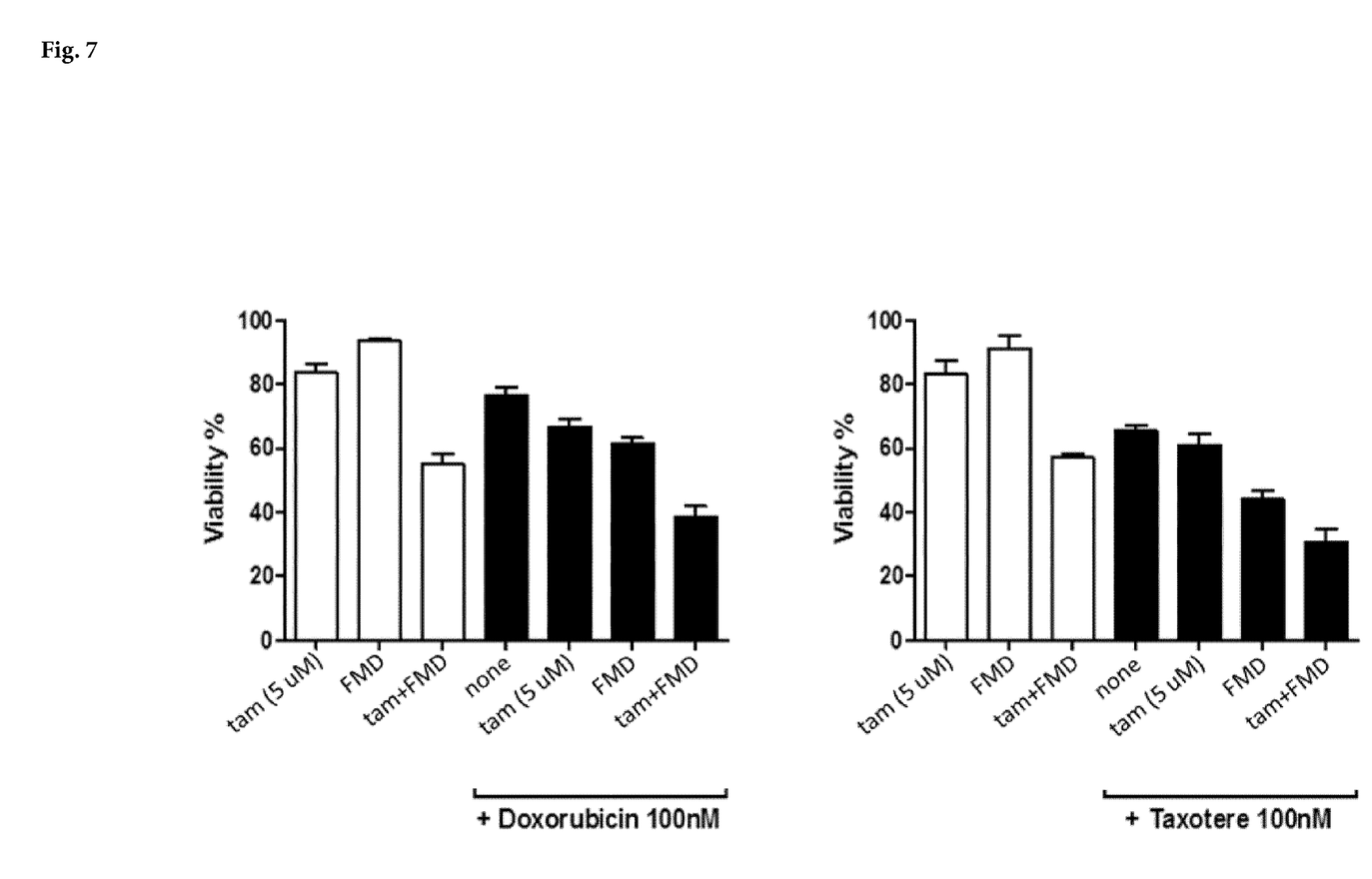
FIG. 7 comprises two histograms showing
1) the respective effects of fasting mimicking conditions or of a fasting-mimicking diet (1% fetal calf serum and 50 mg/dl glucose–FMD), tamoxifen (5 μM), FMD+ tamoxifen (5 μM), tamoxifen 50 μM+doxorubicin 100 nM, FMD+doxorubicin 100 nM and FMD+tamoxifen 5 μM+doxorubicin 100 nM on the viability of the ER-positive BC cells, MCF7.

In the experiment of FIG. 7, $5 \times 10^3$ MCF7 cells/well were plated in 96-well plates in regular DMEM medium containing 10% FBS. 24 h later, the cell medium was removed and cells were incubated for 24 h either in the same medium or in low-glucose (0.5 g/L) DMEM medium containing 1% FBS (fasting mimicking conditions). 24 h later, 10 μM tamoxifen (Tam) was added to the culture medium where indicated. 24 h later, cells were stimulated with doxorubicin or Taxotere at the indicated concentrations. Viability was determined 72 h later in sulforhodamine B assays.

Based on these data, initial proof-of-concept (PoC) experiments in MCF7 xenografts were performed to determine whether short course of fasting (48 hours, water only, once a week) would have anticancer activity per se and, most importantly, whether they would potentiate the activity of tamoxifen and of fulvestrant in vivo.

Figure 8:
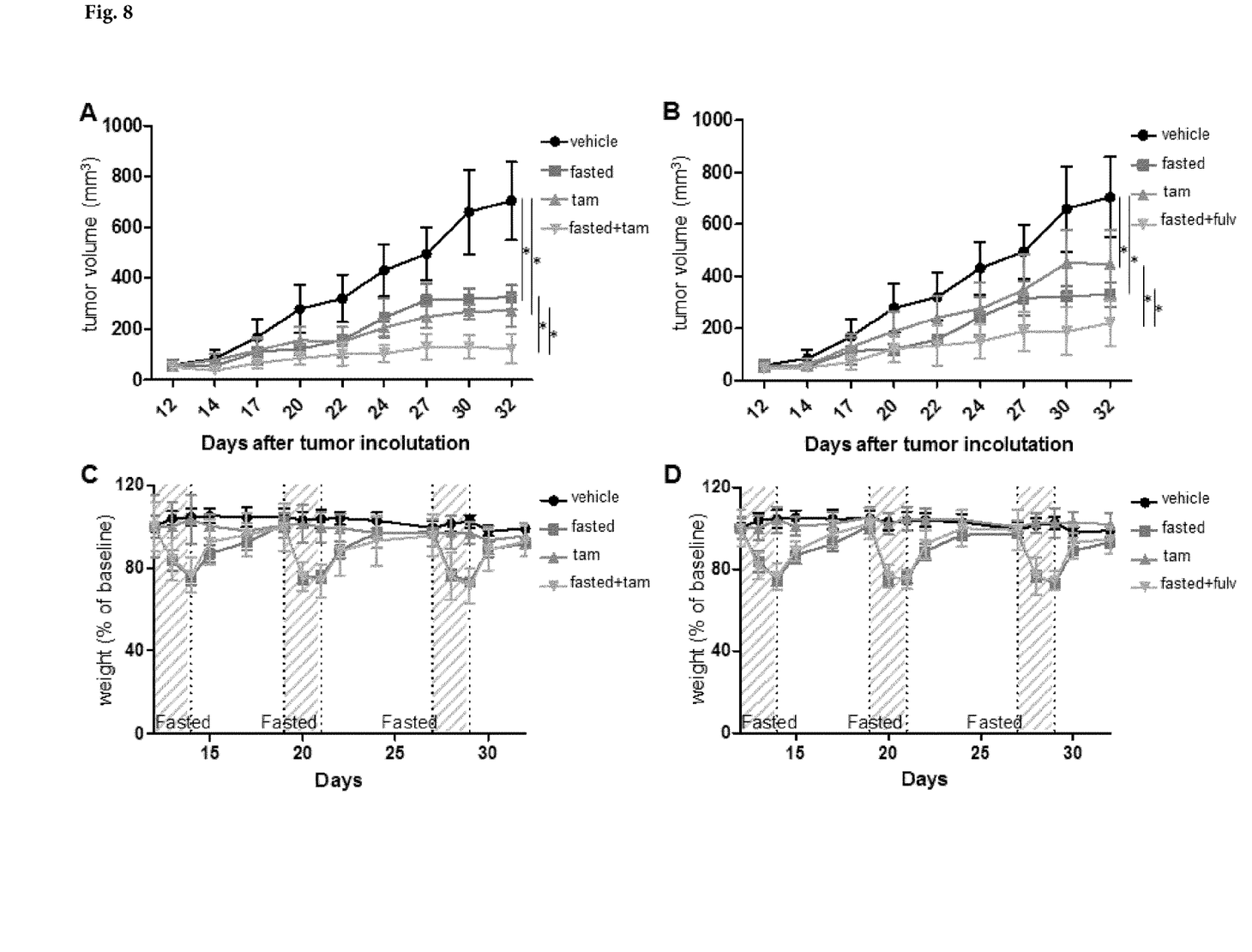
FIG. 8A is a diagram showing the volume of tumors which developed in BALB/c athymic mice (nu+,nu+) following the subcutaneous placement of an estradiol pellet and the injection of MCF7 cells, where the mice were subjected to fasting, treatment with tamoxifen and treatment with tamoxifen+fasting, respectively.
FIG. 8B is a diagram showing the volume of tumors which developed in BALB/c athymic mice (nu+,nu+) following the subcutaneous placement of an estradiol pellet and the injection of MCF7 cells, where the mice were subjected to fasting, treatment with fulvestrant and treatment with fulvestrant+fasting, respectively.
FIG. 8C is a diagram showing the weight of the mice from the experiment of FIG. 8A.
FIG. 8D is a diagram showing the weight of the mice from the experiment of FIG. 8B

Consistent with the in vitro data, both tamoxifen and cycles of fasting reduced the growth of MCF7 xenografts (FIG. 8A, B). However, when combined, the two treatments were significantly more effective than either type of treatment alone.

In the experiment of FIG. 8A-D, 24 h after the subcutaneous placement of an estradiol pellet, six- to eight-week-old BALB/c athymic mice ($nu^+/nu^+$) were injected s.c. with $5 \times 10^6$ MCF7 cells. When tumors became palpable, mouse were randomly assigned to one of six arms (six mice per treatment arm): control (normal diet); tamoxifen (normal diet with tamoxifen, 30 mg/kg/die; oral gavage); fulvestrant (normal diet with fulvestrant, 30 mg/kg once a week; s.c.) fasting (water only, 48 h); fasting+tamoxifen; fasting+fulvestrant. Tumor size (A, B) and mouse weight (C, D) were monitored daily. *: $p<0.05$.

All treatments were well tolerated and, although fasting did lead to a significant weight loss in mouse body weight (FIG. 8C, D), the animals fully recovered their weight between one treatment cycle and the next and addition of tamoxifen to fasting failed to worsen weight losses.

Overall, the above experimental results clearly demonstrate the ability fasting or a fasting-mimicking diet to increase the activity of commonly prescribed hormone therapies for BC, to downregulate ERα in BC cells, and to counter several known mechanisms of hormone therapy resistance. In addition, they clearly demonstrate how combining a hormone treatment with metabolic conditions resulting from fasting or from a fasting-mimicking diet leads to a major impairment in the DNA repair apparatus of cancer cells, sensitizing them to chemotherapeutics.

Thus, a reduced caloric intake through fasting or through a fasting-mimicking diet represents a new approach for increasing the activity of hormonal treatments, for avoiding (or at least markedly delaying) resistance to these agents and, possibly, for preventing tumor-re-growth or for completely eradicating tumor cells when simultaneously applied with hormonal treatments with or without chemotherapy.

REFERENCES

[1] DeSantis C E, Fedewa S A, Goding Sauer A, Kramer J L, Smith R A, Jemal A. Breast cancer statistics, 2015: Convergence of incidence rates between black and white women. CA: a cancer journal for clinicians, 2016; 66: 31-42.

[2] Osborne C K, Schiff R. Mechanisms of endocrine resistance in breast cancer. Annual review of medicine, 2011; 62: 233-47.

[3] Raha P, Thomas S, Thurn K T, Park J, Munster P N. Combined histone deacetylase inhibition and tamoxifen induces apoptosis in tamoxifen-resistant breast cancer models, by reversing Bcl-2 overexpression. Breast cancer research: BCR, 2015; 17: 26.
[4] Creighton C J, Fu X, Hennessy B T, Casa A J, Zhang Y, Gonzalez-Angulo A M, Lluch A, Gray J W, Brown P H, Hilsenbeck S G, Osborne C K, Mills G B, Lee A V, Schiff R. Proteomic and transcriptomic profiling reveals a link between the PI3K pathway and lower estrogen-receptor (ER) levels and activity in ER+breast cancer. Breast cancer research: BCR, 2010; 12: R40.
[5] Baselga J, Campone M, Piccart M, Burris H A, 3rd, Rugo H S, Sahmoud T, Noguchi S, Gnant M, Pritchard K I, Lebrun F, Beck J T, Ito Y, Yardley D, Deleu I, Perez A, Bachelot T, Vittori L, Xu Z, Mukhopadhyay P, Lebwohl D, Hortobagyi G N. Everolimus in postmenopausal hormone-receptor-positive advanced breast cancer. The New England journal of medicine, 2012; 366: 520-9.
[6] Finn R S, Crown J P, Lang I, Boer K, Bondarenko I M, Kulyk S O, Ettl J, Patel R, Pinter T, Schmidt M, Shparyk Y, Thummala A R, Voytko N L, Fowst C, Huang X, Kim S T, Randolph S, Slamon D J. The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study. The Lancet. Oncology, 2015; 16: 25-35.
[7] Lee C, Raffaghello L, Brandhorst S, Safdie F M, Bianchi G, Martin-Montalvo A, Pistoia V, Wei M, Hwang S, Merlino A, Emionite L, de Cabo R, Longo V D. Fasting cycles retard growth of tumors and sensitize a range of cancer cell types to chemotherapy. Science translational medicine, 2012; 4: 124ra27.
[8] Safdie F, Brandhorst S, Wei M, Wang W, Lee C, Hwang S, Conti P S, Chen T C, Longo V D. Fasting enhances the response of glioma to chemo- and radiotherapy. PloS one, 2012; 7: e44603.
[9] Shi Y, Felley-Bosco E, Marti T M, Orlowski K, Pruschy M, Stahel R A. Starvation-induced activation of ATM Chk2/p53 signaling sensitizes cancer cells to cisplatin. BMC cancer, 2012; 12: 571.
[10] Caffa I, D'Agostino V, Damonte P, Soncini D, Cea M, Monacelli F, Odetti P, Ballestrero A, Provenzani A, Longo V D, Nencioni A. Fasting potentiates the anticancer activity of tyrosine kinase inhibitors by strengthening MAPK signaling inhibition. Oncotarget, 2015; 6: 11820-32.
[11] Shim H S, Wei M, Brandhorst S, Longo V D. Starvation promotes REV1 SUMOylation and p53-dependent sensitization of melanoma and breast cancer cells. Cancer research, 2015; 75: 1056-67.
[12] Raffaghello L, Lee C, Safdie F M, Wei M, Madia F, Bianchi G, Longo V D. Starvation-dependent differential stress resistance protects normal but not cancer cells against high-dose chemotherapy. Proceedings of the National Academy of Sciences of the United States of America, 2008; 105: 8215-20.
[13] Brandhorst S, Wei M, Hwang S, Morgan T E, Longo V D. Short-term calorie and protein restriction provide partial protection from chemotoxicity but do not delay glioma progression. Experimental gerontology, 2013; 48: 1120-8.
[14] Yang H, Yang T, Baur J A, Perez E, Matsui T, Carmona J J, Lamming D W, Souza-Pinto N C, Bohr V A, Rosenzweig A, de Cabo R, Sauve A A, Sinclair D A. Nutrient-sensitive mitochondrial NAD+levels dictate cell survival. Cell, 2007; 130: 1095-107.
[15] Lee C, Safdie F M, Raffaghello L, Wei M, Madia F, Parrella E, Hwang D, Cohen P, Bianchi G, Longo V D. Reduced levels of IGF-I mediate differential protection of normal and cancer cells in response to fasting and improve chemotherapeutic index. Cancer research, 2010; 70: 1564-72.
[16] Laviano A, Rossi Fanelli F. Toxicity in chemotherapy—when less is more. The New England journal of medicine, 2012; 366: 2319-20.
[17] Safdie F M, Dorff T, Quinn D, Fontana L, Wei M, Lee C, Cohen P, Longo V D. Fasting and cancer treatment in humans: A case series report. Aging, 2009; 1: 988-1007.
[18] Cheng C W, Adams G B, Perin L, Wei M, Zhou X, Lam B S, Da Sacco S, Mirisola M, Quinn D I, Dorff T B, Kopchick J J, Longo V D. Prolonged fasting reduces IGF-1/PKA to promote hematopoietic-stem-cell-based regeneration and reverse immunosuppression. Cell stem cell, 2014; 14: 810-23.
[19] Zona S, Bella L, Burton M J, Nestal de Moraes G, Lam E W. FOXM1: an emerging master regulator of DNA damage response and genotoxic agent resistance. Biochimica et biophysica acta, 2014; 1839: 1316-22.

The invention claimed is:

1. A method of treating estrogen-responsive breast cancer (BC) in a human patient, which method comprises subjecting said patient to reduced caloric intake for a period of 24-190 hours while said patient is being treated with a compound having antiestrogenic activity, wherein said compound is a SERM and is selected among the group consisting of tamoxifen, raloxifene, toremifene, lasofoxifene, ospemifene, arzoxifene and bazedoxifene.

2. The method according to claim 1, wherein said reduced caloric intake is a daily caloric intake reduced by 10-100%.

3. The method according to claim 2, wherein said reduced caloric intake is a daily caloric intake reduced by 50-100%.

4. The method according to claim 2, wherein said reduced caloric intake is a daily caloric intake reduced by 75-100%.

5. The method according to claim 2, wherein said reduced caloric intake is a daily caloric intake reduced by 10-85% and said patient is fed with foods with a high content of monounsaturated and polyunsaturated fats and a reduced content of proteins and carbohydrates ($\geq$50% of the calories coming from said fats).

6. The method according to claim 2, wherein said period of reduced caloric intake is of 48 to 150 hours.

7. The method according to claim 1, wherein said period of reduced caloric intake with concurrent administration of the compound having antiestrogenic activity to the patient is repeated one or more times after respective periods of 5-60 days, during which said patient is given the compound having antiestrogenic activity while following a diet involving a regular caloric intake.

8. The method according to claim 1, wherein said reduced caloric intake corresponds to less than 300 kcal/day.

9. The method accord to claim 1, wherein said reduced caloric intake corresponds to 100-200 Kcal/day.

10. The method according to claim 8, wherein said reduced caloric intake is obtained by fasting or by means of dietetic food with reduced caloric and/or protein content but containing all necessary micronutrients to prevent malnutrition.

11. A method of treating breast cancer (BC) estrogen-responsive in a human patient, which method comprises feeding said patient only with foods with a high content, of monounsaturated and polyunsaturated fats and a reduced content of proteins and carbohydrates ($\geq$50% of the calories coming from said fats), in such an amount as to ensure a regular daily caloric intake, for a period of 24-190 hours, while said patients is being treated with a compound having antiestrogenic activity, wherein said compound is a SERM and is selected among the group consisting of tamoxifen, raloxifene, toremifene, lasofoxifene, ospemifene, arzoxifene and bazedoxifene.

* * * * *